United States Patent [19]

Kennedy et al.

[11] Patent Number: 5,217,717
[45] Date of Patent: Jun. 8, 1993

[54] METHOD OF MAKING SOYBEAN BOWMAN-BIRK INHIBITOR CONCENTRATE AND USE OF SAME AS A HUMAN CANCER PREVENTATIVE AND THERAPY

[75] Inventors: Ann R. Kennedy, Wynnewood, Pa.; Bernard F. Szuhaj, Fort Wayne, Ind.

[73] Assignees: Central Soya Company, Inc., Fort Wayne, Ind.; The Trustees of the University of Pennsylvania, Philadelphia, Pa.

[21] Appl. No.: 824,719

[22] Filed: Jan. 17, 1992

Related U.S. Application Data

[63] Continuation of Ser. No. 579,155, Sep. 6, 1990, abandoned.

[51] Int. Cl.⁵ .................... A61K 35/78; A61K 47/00; B11B 1/00; A23L 1/20
[52] U.S. Cl. .................... 424/195.1; 514/783; 426/430
[58] Field of Search .................... 424/195.1; 260/412, 260/412.2, 412.4; 426/430; 514/783

[56] References Cited

U.S. PATENT DOCUMENTS

| | | | |
|---|---|---|---|
| 3,365,440 | 1/1968 | Circle et al. | 260/123.5 |
| 3,408,374 | 10/1968 | Cavanagh | 260/412.4 |
| 3,520,868 | 7/1970 | Henderson | 260/112 |
| 3,630,753 | 12/1971 | Melnychyn | 99/17 |
| 4,410,554 | 10/1983 | Sailer | 426/302 |
| 4,435,438 | 3/1984 | Lehnhardt | 426/656 |
| 4,793,996 | 12/1988 | Kennedy | 424/195.1 |
| 4,985,543 | 1/1991 | Sugita | 530/396 |

OTHER PUBLICATIONS

Bowman Proc. Soc. Exptl. Med., 63:547 (1946).
Yavelow et al. Proc. Natl. Acad. Sci., USA 82:5395-5399 (1985).
Weed et al. Carcinogenesis, 6:1239-1241 (1985).
Yavelow et al. Cancer Res., 43:2454-2459 (1983).
Hwang et al. Biochim. Biophys. Acta, 495:369-382 (1977).
Messadi et al. JNCI, 76:447-452 (1986).
Baturay et al. Cell Biology and Toxicology, 2:21-32 (1986).
Kennedy et al. Anticarcinogenic Actions of Protease Inhibitors edited by Cerutti et al., Plenum Pub. Co., pp. 285-295 (1987).
St. Clair et al. Cancer Res., 50:580-586 (1990).
Perlman et al. Methods in Enzymology, 19:860-861 (1970).
Salley, J. Dent. Res., 33:253-262 (1954).
Morris J. Dent. Res., 40:3-15 (1961).
Kassell, Methods Enzymol, 19:860-862.
Birk et al. Biochim. Biophys. Acta, 67:326 (1963).
Kassell, B., "Trypsin and Chymotrypsin Inhibitors from Soybeans", Methods in Enzymology, Proteolytic Enzymes, vol. XIX:853-863 (1970).
Dipietro, C. M. and Liener, I. E. (1989), "Soybean Protease Inhibitors in Foods", J. Food Sci. 54(3):606-617.

(List continued on next page.)

Primary Examiner—Michael G. Wityshyn
Assistant Examiner—Ralph Gitomer
Attorney, Agent, or Firm—Woodcock Washburn Kurtz Mackiewicz & Norris

[57] ABSTRACT

A method for preparing a Bowman-Birk inhibitor (BBI) from soybeans comprising diluting soybean solubles with water, separating purified soybean solubles from the soluble starting material, diluting the purified solubles with water and then ultrafiltrating to produce a crude BBI concentrate which is diluted with water and then spray dried to produce a BBI concentrate product is provided. In another embodiment of the invention, ultrafiltration is eliminated by starting with soy solubles and applying acetone treatment. BBI concentrate product produced in accordance with the invention is a significantly improved inhibiter of malignant cell transformation and methods for its administration to prevent or inhibit progression of cancer are provided.

15 Claims, 3 Drawing Sheets

OTHER PUBLICATIONS

Diepietro, C. M. and Liener, I. E. (1989), "Heat Inactivation of the Kunitz and Bowman-Birk Protease Inhibitors", J. Agric. Food Chem. 37:39–44.

Sessa, D. J. and Bietz, J. A. (1986), "Toasted Soybean Flour Components with Trypsin Inhibitor Activity", JAOCS 63(6):784–788.

Odani S., T. Koide, T. Ono (1986), "Wheat Germ Trypsin Inhibitors", J. Biochem. 100:975-983.

Suzuki A., et al. (1987), "The Structure of Bowman-Birk Type Protease Inhibitor A-II from Peanut (Arachis hypogaea) at 3.3 Å Resolution", J. Biochem. 101:267-274.

Tan-Wilson, A. L. (1988), "Subclassification of Soybean Bowman-Birk Isoinhibitors", JAOCS 65(9):1475-1478.

Norioka N., et al. (1988), "Distribution of the Kunitz and the Bowman-Birk Family Proteinase Inhibitors in Leguminous Seeds", Agric. Biol. Chem. 52(5):1245-1252.

Billings P. C., et al. (1988), "Potential Intracellular Target Proteins of the Anticarcinogenic Bowman Birk Protease Inhibitor Identified by Affinity Chromatography", Can Res. 48:1798-1802.

Ando S., et al. (1987) "Anti-chymotrypsin and Anti--elastase Activities of a Synthetic Bicyclic Fragment Containing a Chymotrypsin-reactive Site of Soybean Bowman-Birk Inhibitor", Biochimica et Biophysica Acta 916:527-531.

Tan-Wilson A. L., et al. (1987) "Soybean Bowman-Birk Trypsin Isoinhibitors", J. Agric. Food Chem. 35:974-981.

Flecker, P. (1987) "Chemical Synthesis, Molecular Cloning and Expression of Gene Coding for a Bowman-Birk-type Proteinase Inhibitor", Eur. J. Biochem. 166:151-156.

Yavelow, J. (1987) "Possible Mechanisms of Action of the Anticarcinogenic Protease Inhibitors", Proc. AACR 28:569.

Wei, C. H. (1983) "Crystallization of Two Cubic Forms of Soybean Trypsin Inhibitor E-I, a Member of the Bowman-Birk Inhibitor Family", J. Biol. Chem. 15:9357-9359.

Joubert, F. J. (1983) "Purification and Some Properties of a Proteinase Inhibitor From Abrus precatorius Seed", Int. J. Biochem. 15(8):1033-1038.

Joubert, F. J. (1984) "Proteinase Inhibitors from Lonchocarpus Capassa (Apple-Leaf) Seed", Biochem. 23(5):957-961.

Tan-Wilson, A., S. E. Cosgriff, M. C. Duggan, R. S. Obach and K. Wilson, "Bowman-Birk Proteinase Isoinhibitor Complements of SoyBean Strains," J. Agr. Food Chem. 133:389-393 (1985).

Birk, Y. (1985), "The Bowman-Birk Inhibitor", J. Peptide Protein Res. 25:113-131.

Foard, D. E., et al. (1982) "In Vitro Synthesis of the Bowman-Birk and Related Soybean Protease Inhibitors", Plant Molec. Biol. 1:227-243.

Norioka, et al. (1982) "Purification and Characterization of Protease Inhibitors From Peanuts (Arachis hypogaea)", J. Biochem. 91:1427-1434.

Nishino, N., and N. Izumiya (1982) "Anti-tryptic Activity of a Synthetic Bicyclic Fragment of Soybean Bowman-Birk Inhibitor", Biochimica et Biophysica Acta 708:233-235.

Foard, D. E., et al. "In Vitro Synthesis of Bowman-Birk and Related Soybean Proteinase Inhibitors".

Spencer, R. W., et al. "Molecular Cloning and Analysis of Sequences Coding for the Bowman Birk and Related Soybean Protease Inhibitors", Plant Physiol. 69(4 Suppl) 140 (1982).

Townshend, G. S., et al. (1982), "Properties of Framgents Prepared from Bowman-Birk Inhibitors" Biochimica et Biophysica Acta 701:346-356.

Johnson, L. A., et al. (1980) "Inactivation of Trypsin Inhibitors in Aqueous Soybean Extracts by Direct Steam Infusion", Cereal Chem. 57(6): 376-379.

Terada, S., et al. (1980), "Studies on the Synthesis of Protease Inhibitors" Int. J. Peptide Protein Res. 15:441-454.

Laskowski, M., Jr., and I. Kato (1980), "Protein Inhibitors of Proteinases", Ann. Rev. Biochem. 49:593-626.

Odani, S. and T. Ikenaka (1978), "Studies on Soybean Trypsin Inhibitors", J. Biochem. 83:747-753.

Odani, S. and T. Ikenaka (1977), "Studies on Soybean Trypsin Inhibitors", J. Biochem. 82:1513-1522.

Nishino, N., H. Aoyagi, T. Kato, and N. Izumiya (1977), "Studies on the Synthesis of Proteinase Inhibitors", J. Biochem. 82:901-909.

Madar, Z., Y. Birk, and A. Gertler "Intestinal Absorption of Soybean Bowman-Birk Trypsin Inhibitor", Israel J. Med. Sci. 13:926 (1977).

Birk, Y., "Trypsin and Chymotrypsin Inhibitors From Soybeans", Methods in Enzymology, Proteolytic Enzymes, Part B. vol. XLV:700–707 (1977).

Birk, Y., "Proteinase Inhibitors from Legume Seeds", Methods in Enzymology, Proteolytic Enzymes, Part B. vol. XLV:697-700 (1977).

Turner, R., et al. (1975), "Equilibria of Bowman-Birk Inhibitor Association with Trypsin and —Chymotrypsin", Biochem. 14(2):275-282.

Nishino, N., H. Aoyagi, T. Kato, and N. Izumiya (1974), "Synthesis and Acitvity of Nonapeptide Fragements of Soybean Bowman-Birk Inhibitor", Experientia 31(4):410–411.

Hogle, J. M. and I. E. Liener (1973), "Reduction and Reactivation of the Bowman-Birk Soybean Inhibitor", Can. J. Biochem. 51:1014–1020.

Odani, S. and T. Ikenaka (1973), "Scission of Soybean Bowman-Birk Proteinase Inhibitor Into Two Small Fragments Having Either Trypsin or Chymotrypsin Inhibitory Activity", J. Biochem. 74:857–860.

Seidl, D. S. and I. E. Liener (1972), "Isolation and Properties of Complexes of the Bowman-Birk Soybean Inhibitor with Trypsin and Chymotrypsin", J. Biolog. Chem. 247(11):3533-3538.

(List continued on next page.)

OTHER PUBLICATIONS

Catsimpoolas, N., "Isoelectric Focusing in Narrow pH Gradients of Kunitz and Bowman-Birk Soybean Trypsin Inhibitors", Sep. Sci. 4(6):483-492.

Steiner, R. F. and V. Frattali (1969), "Purification and Properties of Soybean Protein Inhibitors of Proteolytic Enzymes", J. Agric. Food Chem. 17(3):513-518.

Shklar, G., "Experimental Oral Pathology in the Syrian Hamster", *Progr. Exp. Tumor Res.*, 16:518-538.

Heidelberger, C. "Chemical Carcinogenesis", *Ann. Rev. Biochem.*, 44:79-121 (1975).

Heidelberger, C. and S. Mondal, "In Vitro Chemical Carcinogenesis", pp. 83-92, *Carcinogins: Identification and Mechanisms of Action,* A. Clark Griffin and C. R. Shaw, eds., Raven Press, (New York 1979).

Heidelberger, C. "Assays for In Vitro Carcinogenesis Initiation, and Promotion", pp. 61-63, 65, 67, *The Scientific Basis of Toxicity Assessment,* H. Witachi, ed., Elsiever/North Holland Biomedical Press (1980).

Official Publication 1990 Association of American Feed Control Officials Incorporated.

FIG. 1

Number of Tumors Observed in the Various Treatment Groups
(Histogram Form of Data Presented in Table 1)

METHOD OF MAKING SOYBEAN BOWMAN-BIRK INHIBITOR CONCENTRATE AND USE OF SAME AS A HUMAN CANCER PREVENTATIVE AND THERAPY

INTRODUCTION

The invention described herein was made in the course of research supported in part by the National Institutes of Health under grant numbers NIH-5-R37-CA 22704-13; NIH 7-RO1-CA 34680-07; and NIH 7-U01-CA 46496-02. The Government has certain rights in this invention.

This is a continuation of application Ser. No. 579,155, filed Sep. 6, 1990, now abandoned.

BACKGROUND OF THE INVENTION

This invention relates to the preparation of a Bowman-Birk Inhibitor Concentrate (BBIC) from the soybean. BBIC has been shown to exhibit inhibitory activity against the malignant transformation of cells under certain conditions and its administration to affect various forms of cancer.

It has been shown that the enzyme-inhibitor described by Bowman (*Proc. Soc. Exptl. Med.*, 63:547 (1946)) and Birk et al. (*Bull. Res. Council Israel*, Sec. A 11:48 (1962) and *Biochim. Biophys Acta*, 67:326 (1963)), and subsequently referred to as the Bowman-Birk Inhibitor (BBI), possesses certain physiological activity that prevents, or at least greatly reduces, radiologically or chemically induced malignant transformation of cells in culture and in experimental animals.

Yavelow et al. (*Proc. Natl. Acad. Sci.*, USA 82:5395-5399 (1985)) reported that a crude soybean extract, if defatted with acetone, effectively blocked cell transformation in vitro. An active component of this crude extract is the BBI. These observations, with epidemiological data, suggested BBI as a putative dietary anticarcinogen, particularly with respect to colon cancer.

Weed et al. (*Carcinogenesis*, 6:1239-1241 (1985)) disclose that an extract of soybeans containing the Bowman-Birk protease inhibitor added to the diet of dimethylhydrazine (DMH)-treated mice resulted in a significant suppression of odenomatous tumors of the colonic mucosa. DMH-induced colon cancer in mice is generally regarded as an excellent animal model for the human disease, with carcinogen treatment inducing adenocarcinomas of the colon and rectum which are similar to the tumors arising in the human colon suggesting the possibility that a dietary additive of the sort studied might confer some protection against the development of human colon cancer without undesirable side effects. The BBI extract and methods for its preparation were as described by Yavelow et al. *Cancer Res.*, 43:2454-2459 (1983); *Proc. Natl. Acad. Sci.*, USA 82:5395-5399 (1985) and Hwang et al. *Biochim. Biophys. Acta*, 495:369-382 (1977).

Messadi et al. (*JNCI*, 76:447-452 (1986)) demonstrated that a soybean extract containing the protease inhibitor BBI suppresses 7,12-dimethyl-benz[a]anthracene (DMBA)-induced carcinogenesis in the hamster cheek pouch. This oral cancer model, with the use of the hamster cheek pouch carcinogenesis system, has the same histopathology, growth pattern, and precancerous lesions as the most common form of human oral cancer, squamous cell carcinoma. It was shown in this study that hamster cheek pouch carcinogenesis can be inhibited by BBI and suggested that human oral carcinogenesis might respond to BBI in a comparable manner. The BBI preparation used in this study was a crude extract of the inhibitor prepared as described by Yavelow et al. (*Proc. Natl. Acad. Sci.*, USA 82:5395-5399 (1985)).

Baturay et al. (*Cell Biology and Toxicology*, 2:21-32 (1986)) disclose that a BBI preparation, wherein a crude soybean extract is defatted with acetone, suppresses radiation and chemically induced transformation in vitro. with or without enhancement by the co-carcinogen, pyrene. Yavelow et al., 1985, show that either pure BBI or the BBI extract prepared in accordance with their methods suppresses radiation induced transformation in C3H10T½ cells. Kennedy et al, 1984, report that either pure BBI or the BBI extract prepared in accordance with their method reduce the levels of chromosome abnormalities in cells of patients with Bloom's syndrome (a genetic disease in which the high levels of chromosome abnormalities are thought to predispose the patients to a higher than normal cancer incidence). Still, other studies suggest that soybean-derived protease inhibitors can have suppressive effects on skin, breast and liver carcinogenesis in vivo.

Kennedy et al. in *Anticarcinooenesis and Radiation Protection*, edited by Cerutti et al., Plenum Pub. Co., pp. 285-295 (1987), disclose that BBI suppresses carcinogenesis in various systems using a crude BBI extract prepared by defatting soybeans with acetone. Their results suggested that very low concentrations of BBI-type protease inhibitor preparations would be effective as chemopreventative agents for colon cancer. There was no evidence to suggest that the use of protease inhibitors as chemopreventative agents would be complicated by possible toxicity problems.

St. Clair et al. (*Cancer Res.*, 50:580-586 (1990)) report that the addition of 0.5% or 0.1% semi-purified BBI or 0.1% or 0.01% purified BBI to the diet of DMH-treated mice resulted in a statistically significant suppression of angiosarcomas and nodular hyperplasia of the liver and colon carcinogenesis. The results of this study also indicate that BBI, included as 0.5% of the diet or less had no adverse effect upon the health of the mice but had the capacity to suppress liver and colon carcinogenesis.

Perlmann et al. (*Methods in Enzymology*, 19: 860-861 (1970)) have described an elaborate method for obtaining the BBI from a defatted soybean extract.

U.S. Pat. No. 4,793,996 (Kennedy et al.) discloses a process comprising treating soybeans with acetone, followed by ethanol extraction and acetone precipitation for obtaining BBI. The soybeans may be defatted prior to acetone treatment. In addition, BBI may be further purified by conventional techniques. Kennedy et al. discovered that in the conventional process for preparing BBI from soybeans, a factor remained which adversely affected the ability of BBI to inhibit the malignant transformation of cells. If the factor was removed, the resulting BBI product was capable of inhibiting the malignant transformation of cells. It was found to be possible to remove this factor by treating the soybeans with acetone prior to the ethanol extraction step taught by Perlmann et al.

Kennedy et al. teach that it is unnecessary to carry out a procedure requiring complete purification of the extract to the point where the product contains only a single protein, but instead it has been found effective to stop the purification procedure at a point where a crude inhibitor extract is obtained. This crude extract (i.e., concentrate) is itself edible and can be used as an inhibitor of malignant transformation of cells, for example by oral ingestion. Kennedy et al. disclose a process for preparing a crude soybean extract containing an inhibitor of malignant cell transformation which comprises defatting soybeans and extracting said inhibitor from said defatted soybeans; the improvement comprises defatting said soybeans by bringing them into contact with at least an equal weight of acetone and, thus, producing a crude inhibitor extract having greatly increased effectiveness.

The prior art has not described concentration of BBI from soybean solubles by centrifugation and ultrafiltration, and further purification by acetone precipitation. The separation of soybean solids from hexane-extracted soy flour/flakes in a commercial soy protein concentrates process is well known. However, producing a BBI concentrate by these steps alone i.e., without the use of an aqueous alcohol extraction, is both novel and unexpected.

Furthermore, the less solvent used, the more economical and safer the process. Producing waste-solvent streams containing a mixture of alcohol-water-acetone requires very complex and expensive distillation equipment, which is eliminated in the present invention. It has also been discovered that ultrafiltration is much more efficient than dialysis; one single step of ultrafiltration can remove more solids than 3 days of dialysis. After purification, most of the examples of the present invention employ spray-drying, which is much faster and hence, more economical than the lyophilization described in the prior art. Unexpectedly, spray-drying has no effect on BBI recovery, as measured by chymotrypsin inhibition (CI), used as an indicator for the presence of BBI.

It was also discovered that ultrafiltration step(s) can be avoided altogether when the starting material is soy solubles and the acetone treatment is applied to a substrate that has a substantially higher concentration of BBI than that in the defatted soy flour/flake of the prior art, for example, Kennedy et al.

SUMMARY OF THE INVENTION

In the process of the present invention, an effective BBIC is produced with a high level of biological activity as measured by CI content and/or the inhibition of radiologically or chemically induced malignant transformation of cells. The method of the invention utilizes soybean solubles as a source material that can be recovered directly from a commercial acid-leached soy protein concentrate process. The soybean solubles are diluted with water to 15-25% solids content, followed by centrifugation to produce "purified" soybean solubles. The "purified" solubles are then diluted to 10-12% solids with water to produce reslurried "purified" soybean solubles. The reslurried solubles are then subjected to ultrafiltration to produce a "crude" BBI concentrate. The crude concentrate is then diluted with water and spray dried to produce a BBI concentrate product. In another embodiment of the invention, the diluted crude BBI concentrate is subjected to another ultrafiltration step to produce a "semi-crude" BBI concentrate which is then spray dried to produce a BBI concentrate product. In the preferred embodiment, the semi-crude BBI concentrate is treated with acetone to produce a BBI concentrate precipitate. After settling and decanting the resulting "purified" BBI concentrate precipitate is air dried, ground, reslurried with water, filtered and then lyophilized or spray dried to produce a BBI concentrate product.

In yet another embodiment, the time-consuming ultrafiltration step(s) are eliminated by starting with soy solubles and applying the acetone treatment to a substrate that has a substantially higher concentration of BBI than that in the defatted soy flour/flake of the prior art, resulting in a more economical process.

It was surprisingly found that a BBIC produced in accordance with the method of the invention is a significantly improved inhibitor of malignant cell transformation over prior art BBI products. Methods for the administration of said BBIC to inhibit the malignant transformation of cells and to prevent or inhibit the progression of cancer are also provided.

DETAILED DESCRIPTION OF THE INVENTION

In accordance With the present invention, soybean solubles are diluted with water to 18% solids and then centrifuged to produce "purified" soybean solubles. The purified solubles are diluted with water to 8% solids to produce reslurried "purified" soybean solubles which are subjected to ultrafiltration (1,000 m.w. membrane). The resulting crude BBI concentrate is diluted with water (1:1) and then subjected to a second ultrafiltration step (1,000 m.w. membrane) to produce a "semi-crude" BBI concentrate. The semi-crude concentrate is treated with acetone (2.2:1) to produce a BBI concentrate precipitate. After settling and decanting, the resulting "purified" BBI concentrate precipitate is air dried, ground, reslurried with water to 15% solids, filtered (Buchner funnel/Whatman #1) and then lyophilized to produce a BBI concentrate product.

In another embodiment of the invention, "purified" soybean solubles are produced as described above and then diluted to 10% solids. The resulting reslurried "purified" soybean solubles are then treated as described in the foregoing to produce a "semi-crude" BBI concentrate which is treated with acetone (1.66 to 1) to produce a BBI concentrate precipitate. A BBI concentrate is produced as described above, with the exception that the filtered precipitate is spray dried rather than lyophilized.

In still another embodiment of the invention, soybean solubles are diluted with water to 15-20% solids and centrifuged to produce "purified" soybean solubles. The purified solubles are diluted with water to 10% solids to produce reslurried "purified" soybean solubles which are subjected to ultrafiltration (1,000 m.w. membrane). The resulting "crude" BBI concentrate is diluted with water (1:1) and spray dried to produce a BBI concentrate product. soybean solubles are diluted with water to 16% solids and centrifuged to produce "purified" soybean solubles. The "purified" solubles are diluted with water to 10% solids. The resulting reslurried "purified" solubles are then subjected to ultrafiltration (10,000 m.w. membrane), producing a crude BBI concentrate. The crude concentrate is diluted with water (1:1) and again subjected to ultrafiltration (1,000 m.w.

membrane) to produce a "semi-crude" BBI concentrate which is spray dried to produce a BBI concentrate product.

In another embodiment of the invention, the ultrafiltration step(s) are eliminated by starting with soy solubles and applying the acetone treatment to a substrate that has a substantially higher concentration of BBI than that in defatted soy flour/flake. Soy bean soluble were centrifuged to produce "purified" soybean solubles. Acetone is added to the supernatant to produce a "crude" BBI concentrate precipitate, which is allowed to settle. The resulting precipitate containing the partially purified BBI is then resuspended in water and centrifuged. Acetone is then added to the supernatant and the resulting water soluble, acetone insoluble precipitate allowed to settle, and then are dried to produce a BBI concentrate product.

It was observed that the BBI concentrate produced in accordance with the method of the present invention is highly effective at suppressing DMBA-induced oral carcinogenesis in hamsters at a concentration of 1.0%. In studies performed with the method of the present invention, it was more effective than BBI prepared by prior methods in the suppression of oral carcinogenesis in hamsters. It has also been discovered in vitro that BBI produced according to the present invention is effective at an order of magnitude lower concentration than BBI produced by prior methods.

Compositions made in accordance with the various embodiments of the inventions are useful for inhibiting the malignant transformation of cells by administering a BBI concentrate produced in accordance with the teachings of the invention. Said compositions are useful for preventing cancer or inhibiting cancer progression in an animal, such as man, by administering said compositions, either alone or in combination with a pharmaceutically acceptable carrier. Oral administration, either as a prophylactic dietary supplement or a pharmaceutical are contemplated by the teachings of the invention.

The following examples illustrate the practice of this invention, and the characterization and utility of products resulting therefrom.

EXAMPLE 1

100 pounds of high-nitrogen-soluble (NSI 72—Nitrogen Solubility Index by A.O.C.S. Method) hexane-extracted soy flour (52%, protein—6.25×N) were weighed into a 100 gallon agitated vessel containing 500 pounds of 60% aqueous 3A ethanol that was maintained at 135±5° F. while under vigorous agitation, for one (1) hour. The suspension was cooled, while maintaining vigorous agitation to 75±5° F., and then allowed to settle overnight. The supernatant was transferred into a clean drum and filtered through a 5 micron bag filter. The filtrate was then adjusted to pH 5.3±0.05 with 1.0N HCl. At this point, 1.8 pounds of acetone was added to each pound of filtrate in the kettle (432 lbs of acetone to 240 pounds of filtrate, without agitation) to precipitate the crude BBI active ingredient. The mix then was stirred mildly to assure uniformity. The thus precipitated solids were allowed to settle for one (1) hour. The supernatant was filtered through a 5 micron bag filter. The precipitate was scraped from the container walls and mixed with the filtered solids from the supernatant. The solids were then resolubilized with water using gentle agitation for 15 minutes at room temperature, and subjected to ultrafiltration in an OSMONICS Ultra-Filtration Unit using a 192T-PS (2,000 MW cut-off). The concentrate fraction containing the BBI was centrifuged and the resulting solid impurities were discarded; the remaining liquid portion was freeze-dried. The yield was 525 g of product with a Chymotrypsin Inhibitor (CI) level of 70.4 mgs/g.

EXAMPLE 2

139 pounds of soybean solubles from an acidic aqueous extraction of hexane-defatted soybeans was diluted to 18% solids with 332 pounds of water. The slurry of the diluted soy solubles was centrifuged to remove insoluble matter, and the partially "purified" solids were further diluted with water to a 8% solids level. These "purified" soy solubles were then subjected to ultrafiltration using a 1,000 MW cut-off membrane at 15 gpm and 105 psig, until 31 gallons of permeate was collected. The liquid containing the crude BBI concentrate was again diluted with 31 gallons of water, and the ultrafiltration step was repeated until an additional 47 gallons of permeate was collected and 45 gallons of a semi-crude BBI concentrate remained.

At this point, 55 gallons of acetone was added to 25 gallons of the concentrate; the BBI concentrate precipitate thus obtained was allowed to settle for 1 hour. The liquid supernatant was then decanted, and the precipitate containing the "purified" BBI concentrate was placed in a Buchner Funnel under vacuum to draw off the excess liquid. The dried precipitate was ground in a Waring blender and reslurried to 15% solids. The reslurried suspension was then allowed to settle and the supernatant was lyophilized. The yield was 8 pounds of product with a Chymotrypsin inhibitor (CI) level of 135.5 mgs/g.

EXAMPLE 3

87.3 pounds of soybean solubles from an acidic aqueous extraction of hexane-defatted soybeans were diluted to 18% solids with 207.5 pounds of water. The slurry was centrifuged to remove the insoluble sludge material; diluted to 8% solids with water; and then subjected to ultrafiltration over a 1,000 MW cut-off membrane at 15 gpm. and 100 psig. 44 pounds of permeate was collected; the crude BBI concentrate was re-diluted with 44 pounds of water, and the ultrafiltration step was repeated. 112 pounds of permeate and 163 pounds of a semi-crude BBI concentrate were collected.

270 pounds of acetone was then added to this semi-crude BBI concentrate, and the precipitated BBI concentrate thus formed was allowed to settle for 1 hour. The liquid was decanted and the precipitate was placed in a Buchner funnel under vacuum to draw off the excess liquid. It was then reslurried with water in a Waring blender, allowed to settle, and the supernatant was spray-dried. The yield was 2.3 pounds of product with a Chymotrypsin (CI) content of 261 mgs/g.

EXAMPLE 4

90 pounds of soybean solubles from an acidic aqueous extraction of hexane-defatted soybeans were diluted to between 15% to 20% of solids with water. (The initial solubles contain 50–60% solids.) The slurry was centrifuged to remove 3–5% of the solids, present as insoluble sludge. The supernatant solution was then diluted with water to 10% solids, and subjected to ultrafiltration over a 1,000 MW cut-off membrane. One (1) pound of high-purity water was added to this fraction containing the crude BBI concentrate for every one (1) pound of permeate that had been removed. The ultrafiltration was considered complete when the solids content had begun to decrease. At that point, the BBI concentrate was spray-dried. The yield was 14 pounds of product with a CI content of 99.2 mgs/g.

EXAMPLE 5

50.2 pounds of soybean solubles from an acidic aqueous extraction of hexane-defatted soybeans was diluted to 16% of solids with 126.2 pounds of water. The slurry was centrifuged to remove 3-5% of the solids, present as insoluble sludge. The supernatant solution was then diluted with water to 10% solids, and subjected to ultrafiltration over a 10,000 MW cut-off membrane. One (1) pound of high-purity water was added to the concentrate fraction for every one (1) pound of permeate that had been removed. When the solids content had begun to decrease in the permeate, the permeate was also subjected to ultrafiltration over a 1,000 MW cut-off membrane. After that, the BBI concentrate was spray-dried. The yield was 2.6 pounds of product with a CI content of 61.9 mgs/g.

EXAMPLE 6

A slurry obtained from the whey protein stream produced during the production of soy protein isolate was treated by ultrafiltration over a 1,000 MW cut-off membrane, as described in Example 4. A total of 157.75 pounds of whey protein solution was used. After ultrafiltration, the BBI concentrate fraction, containing 2.7% solids, was spray-dried. The yield was 1.2 pounds of product, containing 187.8 mgs/g of CI.

EXAMPLE 7

1000 gms of soy solubles with a solids content of 19% from an acidic aqueous extraction of hexane-defatted soybeans were centrifuged to remove insoluble matter. At this point, 2 liters of acetone were added to the supernatant. The crude BBI concentrate precipitate thus obtained was allowed to settle for 1 hour. The liquid supernatant was then decanted. The precipitate containing the partially purified BBI was then resuspended in 200 ml of water and centrifuged to remove matter rendered irreversibly insoluble by acetone. 400 ml of acetone was then added to the supernatant. The water soluble, acetone insoluble precipitate which was formed was allowed to settle for 1 hour. The supernatant was decanted. The major portion of water remaining in the precipitate was removed by resuspending the precipitate in 100 ml of acetone and allowing the precipitate to settle for 30 minutes. The supernatant was decanted. The BBI concentrate precipitate was spread thinly on a tray and allowed to air dry to a free flowing white powder. The yield was 5 gm of product with a chymotrypsin inhibitor level of 200 mgs/g.

EXAMPLE 8

As the C3H10T½ cell transformation assay system was the in vitro system in which BBI was first identified as an anticarcinogenic agent, the C3H10T½ cell transformation assay is used for in vitro transformation studies to evaluate the anticarcinogenic activity of a composition made in accordance with the teachings of the present invention. C3H10T½ cells are a mouse embryo fibroblast cell line which can be transformed in culture by chemicals and radiation. When transformed, the cells pile up, forming densely staining foci against a background monolayer of contact-inhibited cells. The transformed foci are characterized as type II or type III using defined morphological criteria. A very high percentage of type II and III foci are tumorigenic when inoculated into syngeneic or nude mice.

To assay for the inhibition of oncogenic transformation by extracts of soybeans, in the in vitro assay, the following protocol is employed: C3H10T½ cells are seeded, and after 24 hours, treated with 600 R of radiation. Immediately after carcinogen treatment, the medium is changed to complete medium containing the sample of interest (at the highest non-toxic level, to at most 1 mM; we have observed in previous studies that if compounds do not have an effect at this concentration (1 mM) in the medium they will not have an effect at higher levels). Subsequently, the medium is changed at weekly intervals and at 6 weeks. The dishes are fixed and stained and the transformed foci evaluated.

If a new preparation looks promising after being tested for the ability to inhibit transformation in vitro, it is tested for the ability to inhibit carcinogenesis in vitro, specifically 7,12-dimethylbenz(a) anthracene induced oral carcinogenesis in hamsters. The protocol to be utilized for these studies is the same as that described by Messadi et al., 1986.

EXAMPLE 9

One hundred sixty five non-inbred male Syrian hamsters, 4 weeks old and weighing 70-90 g. were obtained from Charles River Breeding Laboratories, Wilmington, Mass. The animals were housed 4 per cage with wood chips for bedding. The environment was controlled with an alternating 12-hour light-dark cycle. Water and Purina Laboratory Chow (#5001; Ralston Purina Co., St. Louis, Mo.) were available ad libitum. The hamsters were divided into 23 groups, 3 groups containing 4 animals each, and 20 groups containing 8 animals each (plus one extra animal in Group 17).

The 3 groups of 4 animals each were treated as follows ("0" time represents the beginning of DMBA treatments):

Group 1—1% BBI (5 times per week) for 0-180 days.

Group 2—1% PBBI (5 times per week) for 0-180 days.

Group 3—Mineral oil (3 times per week) for 0-60 days.

These groups served as controls for the other experimental groups whose treatments are described below:

Group 4—DMBA (3 times per week) for 0-60 days.

Group 5—DMBA (3 times per week) for 0-60 days + 1% BBI (5 times per week) for 0-180 days.

Group 6—DMBA (3 times per week) for 0-60 days + 1% BBI ("Method 8"; the invention described here) (5 times per week) for 0-180 days.

Group 7—DMBA (3 times per week) for 0-60 days + 1% BBI (3 times per week) for 0-180 days.

Group 8—DMBA (3 times per week) for 0-60 days + 1% BBI (one time per week) for 0-180 days.

Group 9—DMBA (3 times per week) for 0-60 days + 1% BBI (5 times per week) for 0-60 days.

Group 10—DMBA (3 times per week) for 0-60 days + 1% BBI (5 times per week) for 0-90 days.

Group 11—DMBA (3 times per week) for 0-60 days + 1% BBI (5 times per week) for 14-90 days.

Group 12—DMBA (3 times per week) for 0-60 days + 1% BBI (5 times per week) for 45-135 days.

Group 13—DMBA (3 times per week) for 0-60 days + 1% BBI (5 times per week) for 90-180 days.

Group 14—DMBA (3 times per week) for 0-60 days + 0.1% BBI (5 times per week) for 0-180 days.

Group 15—DMBA (3 times per week) for 0-60 days+0.01% BBI (5 times per week) for 0-180 days.

Group 16—DMBA (3 times per week) for 0-60 days+0.001% BBI (5 times per week) for 0-180 days.

Group 17—DMBA (3 times per week) for 0-60 days+1% PBBI (5 times per week) for 0-180 days.

Group 18—DMBA (3 times per week) for 0-60 days+0.1% PBBI (5 times per week) for 0-180 days.

Group 19—DMBA (3 times per week) for 0-60 days+0.01% PBBI (5 times per week) for 0-180 days.

Group 20—DMBA (3 times per week) for 0-60 days+0.001% PBBI (5 times per week) for 0-180 days.

Group 21—DMBA (3 times per week) for 0-60 days+1% PBBI (3 times per week) for 0-180 days.

Group 22—DMBA (3 times per week) for 0-60 days+1% PBBI (1 time per week) for 0-180 days.

Group 23—DMBA (3 times per week) for 0-60-days+1% Potato Inhibitor (5 times per week) for 0-180 days.

All treatments were applied topically to the right cheek pouch as described (Salley, *J. Dent. Res.*, 33:253-262 (1954); Morris, *J. Dent. Res.*, 40:3-15 (1961)). Animals were weighed at weekly intervals. DMBA (Sigma Chemical Co., St. Louis, Mo.) was applied in a 0.25% solution in heavy mineral oil (U.S.P.) at a dose of 0.125 mg on the cheek pouch 3 times per week for 8 weeks of treatment (i.e., 0.375 mg/wk); this is a standard protocol for DMBA-induced hamster cheek pouch carcinogenesis (Salley, (1954); Morris, (1961)).

Several preparations of protease inhibitors were used in the studies reported here. BBI is an extract of the inhibitor, "BBI concentrate," that has been described in detail elsewhere (Yavelow, et al., (1985)) and was prepared by Central Soya (Ft. Wayne, Indiana). The extract contains five separate protease inhibitors all of which are very similar to BBI in molecular weight and trypsin inhibitory activity (Kassell, Methods Enzymol; 19:860-862 (1970); Hwang, et al., (1977)). The BBI extract was dissolved in distilled water at a final concentration of 0.001-1.0%. BBI referred to as "Method 8" (M8) and prepared as described in Example 2 herein, was also supplied by Central Soya. PBBI containing BBI which has been purified to near homogeneity and is greater than 95% pure PBBI, was prepared from the BBI concentrate as previously described (Yavelow et al. (1985)). The potato inhibitor extract (Kemin Product No. 068129), enriched in chymotrypsin inhibitor I from potatoes (70% of the extract is the inhibitor), was prepared by Kemin Industries, Inc.

All animals were treated for 20 weeks and then sacrificed by $CO_2$ inhalation. The time between the last application of DMBA and animal sacrifices was approximately 4 months. At the time of autopsy, all organs were examined and any organs having an abnormal appearance were removed for histopathologic analysis. The location of all tumors was noted and the size in mm was recorded. The cheek pouches were carefully examined, photographed, and then prepared for histopathologic analysis. Each pouch was fixed in 10% buffered formalin and embedded in paraffin. Five-micron sections were cut and stained with hematoxylin and eosin.

For each animal of each treatment group, the results of the cheek pouch histopathologic analysis are shown in Table 1.

TABLE 1

| Group/ Treatment | Animal No. | Animals with: Single focus of hyperplasia | Multiple foci of hyperplasia | Papillary hyperplasia | Number of tumors: Sebaceous gland adenomas | Papillomas | Squamous cell carcinomas (i = invasive) | Total Tumors (per animal) | (Mean ± S.E.) |
|---|---|---|---|---|---|---|---|---|---|
| 1-1% BBI | 1 | 0 | 0 | 0 | 0 | 0 | 0 | 0 | 0 |
|  | 2 | 0 | 0 | 0 | 0 | 0 | 0 | 0 |  |
|  | 3 | 0 | 0 | 0 | 0 | 0 | 0 | 0 |  |
|  | 4 | 0 | 0 | 0 | 0 | 0 | 0 | 0 |  |
| 2-1% PBBI | 1 | 0 | 0 | 0 | 0 | 0 | 0 | 0 | 0 |
|  | 2 | 0 | 0 | 0 | 0 | 0 | 0 | 0 |  |
|  | 3 | 0 | 0 | 0 | 0 | 0 | 0 | 0 |  |
|  | 4 | 0 | 0 | 0 | 0 | 0 | 0 | 0 |  |
| 3-Mineral Oil | 1 | 0 | 0 | 0 | 0 | 0 | 0 | 0 | 0 |
|  | 2 | 0 | 0 | 0 | 0 | 0 | 0 | 0 |  |
|  | 3 | 0 | 0 | 0 | 0 | 0 | 0 | 0 |  |
|  | 4 | 0 | 0 | 0 | 0 | 0 | 0 | 0 |  |
| 4-DMBA + 3×/wk (0-60 d) | 1 | 0 | x | 0 | 0 | 1 | 5(i) | 6 | 2.7 ± 0.9 |
|  | 2 | 0 | x | 0 | 0 | 2 | 4(i) | 6 |  |
|  | 3 | 0 | x | 0 | 0 | 0 | 1(i) | 1 |  |
|  | 4 | x(squamous) | 0 | 0 | 0 | 0 | 0 | 0 |  |
|  | 5 | 0 | 0 | 0 | 0 | 0 | 1 | 1 |  |
|  | 6 | 0 | x | 0 | 0 | 1 | 1(i) | 2 |  |
|  | 7 | 0 | 0 | 0 | 0 | 0 | 3(i) | 3 |  |
| 5-DMBA + BBI - 1% 5×/wk (0-180 d) | 1 | 0 | 0 | 0 | 0 | 0 | 2(i) | 2 | 0.6 ± 0.4 |
|  | 2 | 0 | 0 | 0 | 0 | 1 | 0 | 1 |  |
|  | 3 | 0 | 0 | 0 | 0 | 2(squamous) | 0 | 2 |  |
|  | 4 | 0 | 0 | 0 | 0 | 0 | 0 | 0 |  |
|  | 5 | 0 | 0 | 0 | 0 | 0 | 0 | 0 |  |
|  | 6 | 0 | 0 | 0 | 0 | 0 | 0 | 0 |  |
|  | 7 | 0 | 0 | 0 | 0 | 0 | 0 | 0 |  |
|  | 8 | 0 | 0 | 0 | 0 | 0 | 0 | 0 |  |
| 6-DMBA + BBI (M8) - 1% 5×/wk (0-180 d) | 1 | 0 | x(squamuos) | 0 | 0 | 0 | 0 | 0 | 0.3 ± 0.2 |
|  | 2 | 0 | 0 | 0 | 0 | 1 | 0 | 1 |  |
|  | 3 | 0 | 0 | 0 | 1 | 0 | 0 | 1 |  |
|  | 4 | 0 | 0 | 0 | 0 | 0 | 0 | 0 |  |
|  | 5 | 0 | 0 | 0 | 0 | 0 | 0 | 0 |  |
|  | 6 | 0 | 0 | 0 | 0 | 0 | 0 | 0 |  |
|  | 7 | 0 | 0 | 0 | 0 | 0 | 0 | 0 |  |
| 7-DMBA + BBI - 1% | 1 | 0 | x | 0 | 0 | 0 | 0 | 0 | 0.6 ± 0.3 |
|  | 2 | x | 0 | 0 | 0 | 1 | 0 | 0 |  |

TABLE 1-continued

| Group/ Treatment | Animal No. | Animals with: Single focus of hyperplasia | Animals with: Multiple foci of hyperplasia | Papillary hyperplasia | Number of tumors: Sebaceous gland adenomas | Papillomas | Squamous cell carcinomas (i = invasive) | Total Tumors (per animal) | (Mean ± S.E.) |
|---|---|---|---|---|---|---|---|---|---|
| 3×/wk | 3 | 0 | x | 0 | 1 | 0 | 1 | 1 | |
| (0–180 d) | 4 | 0 | 0 | 0 | 0 | 0 | 1(i) | 1 | |
| | 5 | 0 | 0 | 0 | 0 | 1 | 1 | 2 | |
| | 6 | 0 | 0 | 0 | 0 | 0 | 0 | 0 | |
| | 7 | 0 | 0 | 0 | 0 | 0 | 0 | 0 | |
| 8-DMBA + | 1 | 0 | 0 | x | 0 | 1 | 1(i) | 2 | 0.6 ± 0.3 |
| BBI - 1% | 2 | 0 | 0 | 0 | 1 | 0 | 1(i) | 2 | |
| 1×/wk | 3 | 0 | 0 | 0 | 0 | 0 | 1 | | |
| (0–180 d) | 4 | 0 | 0 | 0 | 0 | 0 | 0 | 0 | |
| | 5 | 0 | 0 | 0 | 0 | 0 | 0 | 0 | |
| | 6 | 0 | 0 | 0 | 0 | 0 | 0 | 0 | |
| | 7 | 0 | 0 | 0 | 0 | 0 | 0 | 0 | |
| | 8 | 0 | 0 | 0 | 0 | 0 | 0 | 0 | |
| 9-DMBA + | 1 | 0 | 0 | x | 0 | 0 | 0 | 1 | 1.8 ± 1.8 |
| BBI - 1% | 2 | 0 | 0 | x(squamous) | 0 | 0 | 0 | 0 | |
| 5×/wk | 3 | 0 | 0 | 0 | 0 | 0 | 11(i) | 11 | |
| (0–60 d) | 4 | 0 | 0 | 0 | 0 | 0 | 0 | 0 | |
| | 5 | 0 | 0 | 0 | 0 | 0 | 0 | 0 | |
| | 6 | 0 | 0 | 0 | 0 | 0 | 0 | 0 | |
| 10-DMBA + | 1 | 0 | x | 0 | 0 | 0 | 0 | 0 | 0.3 ± 0.2 |
| BBI - 1% | 2 | 0 | x | 0 | 0 | 0 | 0 | 0 | |
| 5×/wk | 3 | 0 | 0 | 0 | 0 | 0 | 1(i) | 1 | |
| (0–90 d) | 4 | 0 | 0 | 0 | 0 | 0 | 1 | 1 | |
| | 5 | 0 | x | 0 | 0 | 0 | 0 | 0 | |
| | 6 | 0 | 0 | 0 | 0 | 0 | 0 | 0 | |
| | 7 | 0 | 0 | 0 | 0 | 0 | 0 | 0 | |
| 11-DMBA + | 1 | x | 0 | 0 | 0 | 0 | 1 | 1 | 0.3 ± 0.2 |
| BBI - 1% | 2 | 0 | 0 | 0 | 0 | 1 | 0 | 1 | |
| 5×/wk | 3 | 0 | 0 | 0 | 0 | 0 | 0 | 0 | |
| (14–90 d) | 4 | 0 | 0 | 0 | 0 | 0 | 0 | 0 | |
| | 5 | 0 | 0 | 0 | 0 | 0 | 0 | 0 | |
| | 6 | 0 | 0 | 0 | 0 | 0 | 0 | 0 | |
| | 7 | 0 | 0 | 0 | 0 | 0 | 0 | 0 | |
| 12-DMBA + | 1 | 0 | 0 | 0 | 0 | 1 | 0 | 1 | 0.4 ± 0.2 |
| BBI - 1% | 2 | 0 | 0 | 0 | 0 | 0 | 1 | 1 | |
| 5×/wk | 3 | 0 | 0 | x | 0 | 0 | 1 | 1 | |
| (45–135d) | 4 | 0 | 0 | 0 | 0 | 0 | 0 | 0 | |
| | 5 | 0 | 0 | 0 | 0 | 0 | 0 | 0 | |
| | 6 | 0 | 0 | 0 | 0 | 0 | 0 | 0 | |
| | 7 | 0 | 0 | 0 | 0 | 0 | 0 | 0 | |
| | 8 | 0 | 0 | 0 | 0 | 0 | 0 | 0 | |
| 13-DMBA + | 1 | x | 0 | 0 | 0 | 0 | 0 | 1 | 0.7 ± 0.3 |
| BBI - 1% | 2 | 0 | 0 | x | 0 | 1 | 0 | 1 | |
| 5×/wk | 3 | 0 | 0 | x(squamous) | 0 | 0 | 2(i) | 2 | |
| (90–180 d) | 4 | 0 | 0 | 0 | 0 | 0 | 0 | 0 | |
| | 5 | 0 | 0 | 0 | 0 | 0 | 0 | 0 | |
| | 6 | 0 | 0 | 0 | 0 | 0 | 0 | 0 | |
| 14-DMBA + | 1 | 0 | 0 | 0 | 0 | 0 | 0 | 0 | 0.5 ± 0.5 |
| BBI - 0.1% | 2 | x | 0 | 0 | 0 | 3 | 0 | 3 | |
| 5×/wk | 3 | 0 | 0 | x | 0 | 0 | 0 | 0 | |
| (0–180 d) | 4 | x | 0 | 0 | 0 | 0 | 0 | 0 | |
| | 5 | 0 | 0 | 0 | 0 | 0 | 0 | 0 | |
| | 6 | 0 | 0 | 0 | 0 | 0 | 0 | 0 | |
| 15-DMBA + | 1 | 0 | 0 | 0 | 0 | 1 | 0 | 1 | 0.6 ± 0.3 |
| BBI - 0.01% | 2 | 0 | 0 | 0 | 0 | 0 | 2(i) | 2 | |
| 5×/wk | 3 | 0 | 0 | 0 | 0 | 0 | 0 | 0 | |
| (0–180 d) | 4 | 0 | 0 | 0 | 0 | 0 | 1 | 1 | |
| | 5 | 0 | 0 | 0 | 0 | 0 | 0 | 0 | |
| | 6 | 0 | 0 | 0 | 0 | 0 | 0 | 0 | |
| | 7 | 0 | 0 | 0 | 0 | 0 | 0 | 0 | |
| 16-DMBA + | 1 | 0 | 0 | 0 | 0 | 0 | 4(i) | 4 | 0.9 ± 0.6 |
| BBI-0.001% | 2 | x | 0 | 0 | 0 | 0 | 0 | 0 | |
| 5×/wk | 3 | 0 | 0 | 0 | 1 | 0 | 0 | 1 | |
| (0–180 d) | 4 | 0 | 0 | 0 | 0 | 1 | 0 | 1 | |
| | 5 | 0 | 0 | 0 | 0 | 0 | 0 | 0 | |
| | 6 | 0 | 0 | 0 | 0 | 0 | 0 | 0 | |
| | 7 | 0 | 0 | 0 | 0 | 0 | 0 | 0 | |
| 17-DMBA + | 1 | 0 | 0 | x | 0 | 0 | 1 | 1 | 0.2 ± 0.2 |
| PBBI - 1% | 2 | 0 | 0 | 0 | 0 | 0 | 0 | 0 | |
| 5×/wk | 3 | 0 | 0 | 0 | 0 | 0 | 1 | 1 | |
| (0–180 d) | 4 | 0 | 0 | 0 | 0 | 0 | 0 | 0 | |
| | 5 | 0 | 0 | 0 | 0 | 0 | 0 | 0 | |
| | 6 | 0 | 0 | 0 | 0 | 0 | 0 | 0 | |
| | 7 | 0 | 0 | 0 | 0 | 0 | 0 | 0 | |
| | 8 | 0 | 0 | 0 | 0 | 0 | 0 | 0 | |
| | 9 | 0 | 0 | 0 | 0 | 0 | 0 | 0 | |

TABLE 1-continued

| Group/ Treatment | Animal No. | Animals with: Single focus of hyperplasia | Multiple foci of hyperplasia | Papillary hyperplasia | Number of tumors: Sebaceous gland adenomas | Papillomas | Squamous cell carcinomas (i = invasive) | Total Tumors (per animal) | (Mean ± S.E.) |
|---|---|---|---|---|---|---|---|---|---|
| 18-DMBA + | 1 | x | 0 | 0 | 0 | 0 | 0 | 0 | 0.5 ± 0.5 |
| PBBI - 0.1% | 2 | x(squamous) | 0 | 0 | 0 | 0 | 0 | 0 | |
| 5×/wk | 3 | 0 | x | 0 | 0 | 0 | 0 | 0 | |
| (0-180 d) | 4 | 0 | 0 | 0 | 1 | 0 | 3(i) | 4 | |
| | 5 | 0 | x | 0 | 0 | 0 | 0 | 0 | |
| | 6 | 0 | 0 | 0 | 0 | 0 | 0 | 0 | |
| | 7 | 0 | 0 | 0 | 0 | 0 | 0 | 0 | |
| | 8 | 0 | 0 | 0 | 0 | 0 | 0 | 0 | |
| 19-DMBA + | 1 | 0 | x | 0 | 0 | 0 | 3(papillary; i) | 3 | 0.3 ± 0.2 |
| PBBI-0.01% | 2 | 0 | 0 | 0 | 0 | 0 | 0 | 0 | |
| 5×/wk | 3 | 0 | 0 | 0 | 0 | 0 | 0 | 0 | |
| (0-180 d) | 4 | 0 | 0 | 0 | 0 | 0 | 0 | 0 | |
| | 5 | 0 | 0 | 0 | 0 | 0 | 0 | 0 | |
| | 6 | 0 | x(squamous) | 0 | 0 | 0 | 1(i) | 1 | |
| | 7 | 0 | 0 | 0 | 0 | 0 | 0 | 0 | |
| 20-DMBA + | 1 | 0 | x | 0 | 0 | 0 | 0 | 0 | 1.6 ± 1.0 |
| PBBI- | 2 | 0 | 0 | 0 | 0 | 0 | 6(i) | 6 | |
| 0.001% | 3 | 0 | x | 0 | 0 | 2 | 3(i) | 5 | |
| 5×/wk | 4 | 0 | 0 | 0 | 0 | 0 | 0 | 0 | |
| (0-180 d) | 5 | 0 | 0 | 0 | 0 | 0 | 0 | 0 | |
| | 6 | 0 | 0 | 0 | 0 | 0 | 0 | 0 | |
| | 7 | 0 | 0 | 0 | 0 | 0 | 0 | 0 | |
| 21-DMBA + | 1 | 0 | x | 0 | 0 | 0 | 0 | 0 | 0.6 ± 0.4 |
| PBBI - 1% | 2 | 0 | 0 | 0 | 1 | 0 | 1 | 2 | |
| 3×/wk | 3 | 0 | 0 | 0 | 1 | 0 | 1 | 2 | |
| (0-180 d) | 4 | 0 | 0 | 0 | 0 | 0 | 0 | 0 | |
| | 5 | 0 | 0 | 0 | 0 | 0 | 0 | 0 | |
| | 6 | 0 | 0 | 0 | 0 | 0 | 0 | 0 | |
| | 7 | 0 | 0 | 0 | 0 | 0 | 0 | 0 | |
| 22-DMBA + | 1 | x | 0 | 0 | 0 | 1 | 1 | 2 | 0.5 ± 0.4 |
| PBBI - 1% | 2 | 0 | 0 | x | 0 | 0 | 0 | 0 | |
| 1×/wk | 3 | 0 | 0 | 0 | 0 | 1 | 0 | 1 | |
| (0-180 d) | 4 | 0 | 0 | 0 | 0 | 0 | 0 | 1 | |
| | 5 | 0 | 0 | 0 | 0 | 0 | 0 | 0 | |
| | 6 | 0 | 0 | 0 | 0 | 0 | 0 | 0 | |
| 23-DMBA + | 1 | 0 | 0 | 0 | 0 | 1 | 1(i) | 2 | 1.4 ± 0.3 |
| Pot. Inh. - | 2 | 0 | 0 | 0 | 1 | 0 | 1 | 2 | |
| 1% 5×/wk | 3 | 0 | 0 | 0 | 0 | 1 | 0 | 1 | |
| (0-180 d) | 4 | 0 | 0 | 0 | 0 | 0 | 1 | 1 | |
| | 5 | 0 | 0 | 0 | 0 | 0 | 1(i) | 1 | |

Footnotes
1. Abbreviations used:
BBI = BBI concentrate; PBBI = Pure BBI
2. Other Pathology Observed in the Various Treatment Groups:
Group 4, animal 2 = Hyperplastic spleen
Group 9, animal 3 = Hyperplastic spleen
Group 12, animal 5 = kidney nephrosis
Group 14, animal 1 = stomach, squamous papillary hyperplasia
Group 16, animal 1 = Hyperplastic spleen
Group 16, animal 4 = Melanin nodule
Group 18, animal 6 = leukemic node
Group 21, animal 7 = stomach papillomas; lymphoreticular tumor
3. Statistical Analysis (Student's t-test):
Groups 4 vs. 5, $p < 0.05$; 4 vs. 6, $p = 0.02$; 4 vs. 7, $p < 0.05$, 4 vs. 8 $p < 0.05$; 4 vs. 9, $p > 0.05$; 4 vs. 10, $p < 0.02$; 4 vs. 11, $p < 0.02$; 4 vs. 12, $p < 0.05$; 4 vs. 13, $p < 0.10$; 4 vs. 14, $p < 0.05$; 4 vs. 15, $p < 0.05$; 4 vs. 16, $p > 0.05$; 4 vs. 17, $p < 0.01$; 4 vs. 18, $p < 0.05$; 4 vs. 19, $p < 0.02$; 4 vs. 20, $p > 0.05$; 4 vs. 21, $p < 0.05$; 4 vs. 22, $p < 0.05$; 4 vs. 23, $p > 0.05$.

Histopathological alterations observed in organs other than the cheek pouch are also given in Table 1. The data for the tumors of the cheek pouch (given in Table 1) are shown in histogram form in FIG. 1. Examples of hamster cheek pouches with and without tumors are shown in FIG. 2(a) and FIG. 2(b).

Figure 1:
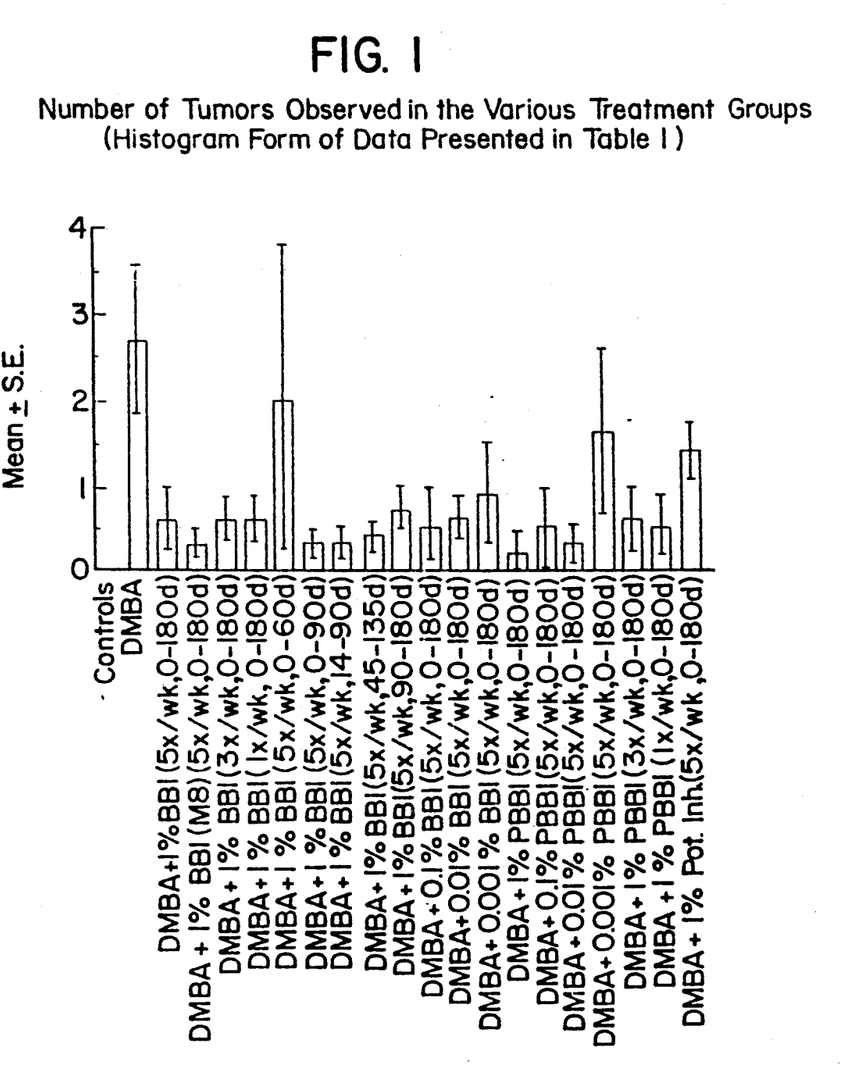
FIG. 1 is a histogram showing the number of tumors observed in the animal study treatment groups.
Figure 2A:
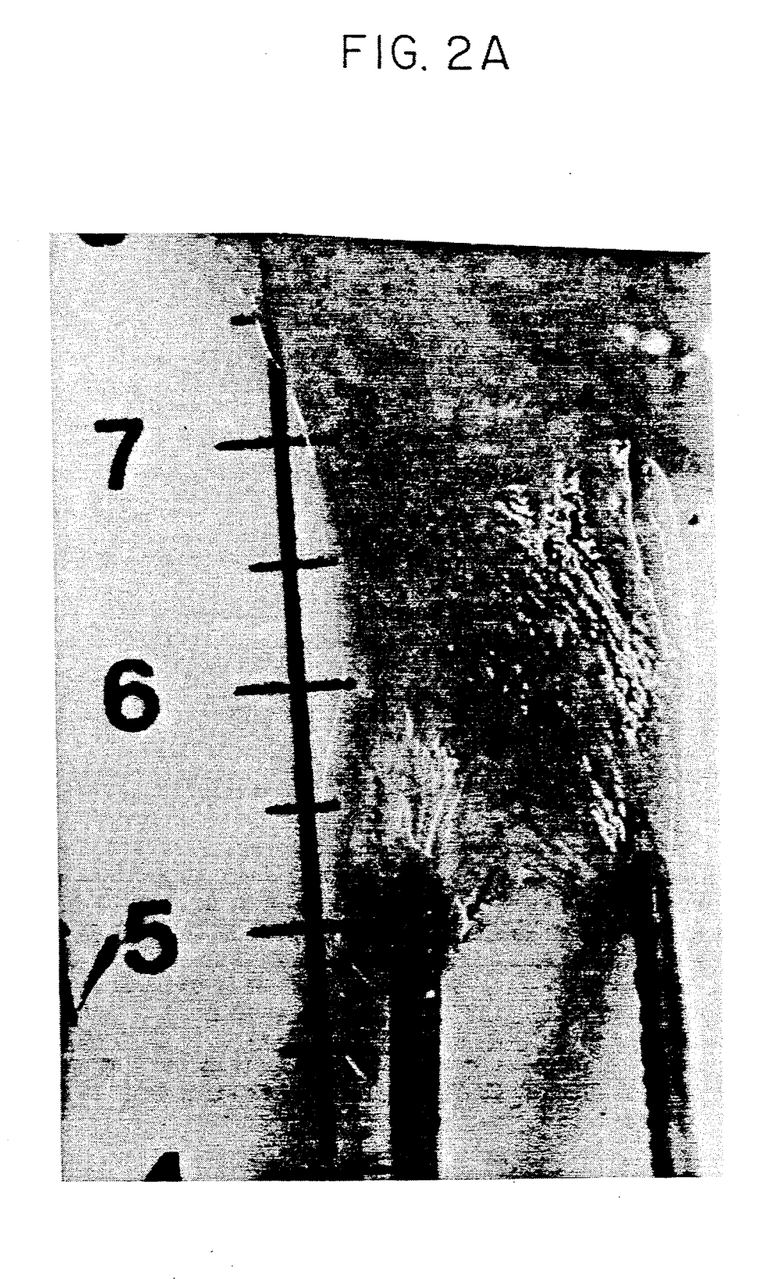
FIG. 2(a) is a photograph of a normal (untreated) hamster cheek pouch.
Figure 2B:
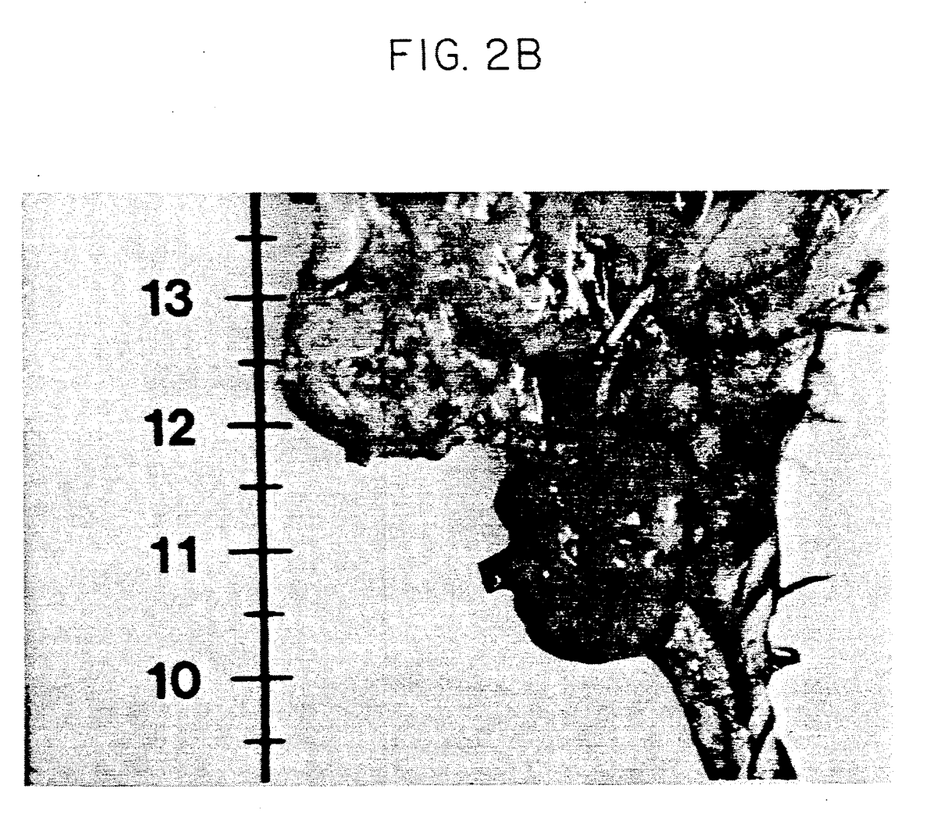
FIG. 2(b) is a photograph showing a DMBA-treated hamster cheek pouch with tumors.

The conclusions that can be drawn from the data shown in Table 1 and FIG. 1 are as follows:

When present for the entire carcinogenesis assay period (0-180 days), BBI significantly suppresses DMBA induced oral carcinogenesis at concentrations from 1% down to 0.01% (Groups 4 vs. 5,6,14 and 15, $p < 0.05$). At 0.001%, the suppression of carcinogenesis by BBI is not statistically significant (Group 4 vs. 16, $p > 0.05$).

2) 1% BBI applications at 5 times per week, 3 times per week and once per week (for the entire carcinogenesis assay period; 0-180 days), led to a significant reduction in the DMBA induced tumor yield (Groups 4 vs. 5, 7 and 8, $p < 0.05$).

3) 1% BBI applications for the following time periods led to a significantly reduced tumor yield: 0-180 days, 0-90 14-90 days and 45-135 days (Groups 4 or 5, 6, 10, 11), $p < 0.05$). Applications of 1% BBI from days 0-60 and 90-180 reduced the DMBA induced tumor yield, but not in a statistically significant manner (Groups 4 vs. 9, $p > 0.5$; Groups 4 vs. 13, $p < 0.10$).

4) The method of the invention BBI, "Method 8", gave results similar to those obtained for the previous method of preparing BBI (at 1% BBI) when applied 5 times per week for 0-180 days; both the previous method of preparing BBI and the new method ("Method 8") led to a significant reduction in the DMBA induced tumor yield (Groups 4 vs. 5, p 0.05; 4 vs. 6, p 0.02). Method 8, however, was more effective than the standard method for preparing BBI, as the results were of higher statistical significance and no malignant tumors were observed with this preparation (squamous cell carcinomas were observed in the animals treated with the standard BBI preparation).

The histopathological analysis showed that there were tumors in all of the experimental groups receiving DMBA treatments. The only DMBA +BBI groups in which no animals had malignant tumors were the groups receiving BBI prepared by the new method of the invention (specifically, group 6—Method 8), and the group receiving 0.1% BBI (group 14).

What is claimed is:

1. A method for preparing a Bowman-Birk inhibitor from soybeans which comprises the steps of:
   (a) removing insolubles from acidic aqueous-extracted hexane-defatted soybeans to produce soybean solubles having a solids concentration of at least 50%;
   (b) adding acetone to said soybean solubles to produce a crude Bowman-Birk inhibitor concentrate;
   (c) diluting said crude Bowman-Birk inhibitor concentrate with water;
   (d) removing insolubles from said diluted crude Bowman-Birk inhibitor concentrate and adding acetone to produce a water-soluble, acetone-insoluble Bowman-Birk inhibitor concentration;
   (e) resuspending said water soluble, acetone-insoluble Bowman-Birk inhibitor concentrate in acetone to produce a BBI concentrate;
   (f) drying said BBI concentrate to produce a BBI concentrate product.

2. A composition comprising a BBI concentrate product produced in accordance with the method of claim 1, either alone or in combination with a pharmaceutically acceptable carrier.

3. The method of claim 1 wherein step (f) is performed by spray drying.

4. A method for preparing a Bowman-Birk inhibitor from soybeans comprising:
   (a) diluting soybean solubles from an acidic aqueous extraction of hexane-defatted soybeans with water to at least 15% solids;
   (b) centrifuging said diluted soybean solubles to produce purified soybean solubles;
   (c) diluting said purified soybean solubles with water to at least 8% solids;
   (d) ultrafiltrating said diluted purified soybean solubles using a 1,000 MW cut-off membrane at about 15 gpm and about 105 psig to produce crude Bowman-Birk inhibitor concentrate;
   (e) diluting said Bowman-Birk inhibitor concentrate with water to about 1:1 w/w;
   (f) repeating step (d);
   (g) adding acetone to the concentrate to about 1.8:1 v/v;
   (h) settling the BBI concentrate precipitate obtained in step (g) for about 1 hour at ambient temperature;
   (i) drying the BBI concentrate precipitate;
   (j) grinding and reslurrying the dried BBI concentrate precipitate to a consistency where the product can be handled;
   (k) settling the reslurried suspension produced in step (j); and
   (l) drying the supernatant produced in step (k) to yield a Bowman-Birk concentrate product having a Chymotrypsin inhibitor level of a minimum of about 125 g BBI/#100 soy solubles.

5. The method of claim 4 wherein the step (l) is performed by spray drying.

6. A Bowman-Birk product comprising a Bowman-Birk concentrate product produced in accordance with the method of claim 4.

7. A method for preparing a Bowman-Birk inhibitor from soybeans in the absence of an alcoholic extraction procedure, consisting essentially of the steps:
   (a) removing insolubles from acidic aqueous-extracted hexane-defatted soybeans to produce soybean solubles having a solids concentration of at least 50%;
   (b) diluting the soybean solubles with an aqueous solution to form a slurry;
   (c) separating the aqueous soluble portion of the soybean solubles from the slurry to form a purified soybean soluble composition;
   (d) diluting the purified soybean soluble composition with an aqueous solution and ultrafiltering the aqueous soluble portion of the diluted purified soybean soluble composition at least once to form a Bowman-Birk inhibitor concentrate; and
   (e) drying the Bowman-Birk inhibitor concentrate and recovering a Bowman-Birk inhibitor product.

8. A Bowman-Birk product comprising a Bowman-Birk inhibitor product produced in accordance with the method of claim 7.

9. The method of claim 7 wherein the drying step is spray drying.

10. The method of claim 9 wherein the slurry of step (b) is a 15 to 20 percent solid solution.

11. The method of claim 9 further comprising diluting the Bowman-Birk inhibitor concentrate with an aqueous solution prior to the spray drying.

12. The method of claim 7 further comprising, prior to the drying step, diluting the Bowman-Birk inhibitor concentrate with acetone and retaining the precipitated acetone insoluble portion.

13. The method of claim 12 wherein the drying step is spray drying.

14. The method of claim 12 further comprising lyophilizing the dried Bowman-Birk inhibitor.

15. The method of claim 12 wherein the slurry of step (b) is a 15 to 20 percent solid solution.

* * * * *